(12) United States Patent
Euting et al.

(10) Patent No.: US 8,846,897 B2
(45) Date of Patent: *Sep. 30, 2014

(54) METHOD FOR FILTERING NUCLEIC ACIDS, IN PARTICULAR FROM FIXED TISSUE

(75) Inventors: Heike Euting, Bocholt (DE); Guido Hennig, Köln (DE); Kerstin Bohmann, Köln (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 219 days.

This patent is subject to a terminal disclaimer.

(21) Appl. No.: 12/997,903

(22) PCT Filed: Jun. 18, 2009

(86) PCT No.: PCT/EP2009/057561
§ 371 (c)(1),
(2), (4) Date: Dec. 14, 2010

(87) PCT Pub. No.: WO2009/153299
PCT Pub. Date: Dec. 23, 2009

(65) Prior Publication Data
US 2011/0092691 A1    Apr. 21, 2011

(30) Foreign Application Priority Data
Jun. 20, 2008  (DE) .......................... 10 2008 029 356

(51) Int. Cl.
*C07H 21/00* (2006.01)
*C12Q 1/68* (2006.01)
*C12N 15/10* (2006.01)

(52) U.S. Cl.
CPC ................... *C12N 15/1013* (2013.01)
USPC ...... 536/25.4; 435/6.1; 536/25.41; 536/25.42

(58) Field of Classification Search
None
See application file for complete search history.

(56) References Cited

U.S. PATENT DOCUMENTS

| | | | |
|---|---|---|---|
| 6,090,546 A * | 7/2000 | Breivik et al. ............... | 435/6.12 |
| 6,194,562 B1 * | 2/2001 | Smith et al. .................. | 536/24.5 |
| 6,284,470 B1 * | 9/2001 | Bitner et al. ................. | 435/6.16 |
| 6,441,152 B1 * | 8/2002 | Johansen et al. ............ | 536/23.1 |
| 2004/0203086 A1 * | 10/2004 | Piasio et al. .................... | 435/11 |
| 2004/0215011 A1 * | 10/2004 | Deggerdal et al. ........... | 536/25.4 |
| 2007/0026432 A1 | 2/2007 | Ke et al. | |
| 2009/0047724 A1 * | 2/2009 | Hillebrand .................... | 435/219 |

FOREIGN PATENT DOCUMENTS

| | | |
|---|---|---|
| EP | 0389063 | 9/1990 |
| WO | WO9831840 A1 * | 1/1998 |
| WO | 00/70040 | 11/2000 |
| WO | 0146402 | 6/2001 |

(Continued)

OTHER PUBLICATIONS

Feng.Transfusion. 2003. 32(9): 850-854.*

(Continued)

*Primary Examiner* — Robert T Crow
*Assistant Examiner* — Joseph G Dauner (57) ABSTRACT

The invention relates to a method for filtering nucleic acids, to a kit for carrying out the method according to the invention and to a novel use of magnetic particles for filtering a biological sample. The method according to the invention comprises the following steps: a) the sample is held in an aqueous solution; b) lysing of the sample; c) separation of cellular debris; and d) the nucleic acids are isolated from the solution, steps (a) to (c) taking place under non-chaotropic conditions.

14 Claims, 4 Drawing Sheets

(56) References Cited

FOREIGN PATENT DOCUMENTS

| WO | 03040364 | 5/2003 |
|---|---|---|
| WO | 03058649 | 7/2003 |
| WO | WO 2007060248 A1 * | 5/2007 |

OTHER PUBLICATIONS

The Engineering Toolbox (retrieved on Jun. 11, 2012 from the internet: <url: http://www.engineeringtoolbox.com/stp-standard-ntp-normal-air-d_772.html>).*

Dynabeads (retrieved on Mar. 13, 2014 from the internet: http://www.lifetechnologies.com/order/catalog/product/11205D).*

Gilbert M Thomas P et al: "The isolation of nucleic acids from fixed, paraffin-embedded tissues—which methods are useful when?" PLOS One, Bd. 2, Nr. 6 2007, Seiten E537/1-E537/12, XP002547508, ISSN:1932-6203.

Sato Y et al: "Comparison of the DNA extraction methods for polymerase chain reaction amplification from formalin-fixed and paraffin-embedded tissues" Diagnostic Molecular Pathology, Bd. 10, Nr. 4, Dec. 1, 2001, Seiten 265-271, XP009010319, New York, NY, US.

Watson R M et al: "Increased sample capacity for genotyping and expression profiling by kinetic polymerase chain reaction" Analytical Biochemistry, Bd. 329, Nr. 1, Jun. 1, 2004, Seiten 58-67, XP004506465 Academic Prss Inc, New York, ISSN: 0003-2697.

Hofmann W P et al: "Comparison of transcription mediated amplification (TMA) and reverse transcription polymerase chain reaction (RT-PCR) for detection of hepatitis C virus RNA in liver tissue" Journal of Clinical Virology, Bd. 32, Nr. 4, Apr. 1, 2005, Seiten 289-293, XP004797283, Elsevier, Amasterdam, NL, ISSN: 1386-6532.

International Search Report for PCT/EP09/057561.

Müller B. M. et al; "Quantitative determination of estrogen receptor, progesterone receptor, and HER2 mRNA in formalin-fixed paraffin-embedded tissue—a new option for predictive biomarker assessment in breast cancer"; Diagnostic Mol Pathol; vol. 20; No. 1; pp. 1-10, (2011).

Bohmann, K. et al., RNA Extraction from archival formalin-fixed paraffin-embedded tissue: am comparison of manual, semiautomated, and fully automated purification methods, Clin. Chemistry 55:9, 1719-1727(2009).

* cited by examiner

40-CT
(RPL37A)

FIG 5

RPL37A (40-CT)

METHOD FOR FILTERING NUCLEIC ACIDS, IN PARTICULAR FROM FIXED TISSUE

The invention relates to a method for purifying nucleic acids, a kit for carrying out the method according to the invention and a novel use of magnetic particles for purifying a biological sample.

Very recently, molecular diagnostics has increasingly gained in importance. It has found an entry into the clinical diagnosis of diseases (inter alia detection of infectious pathogens, detection of mutations of the genome, detection of circulating tumor cells and identification of risk factors for predisposition to a disease). However, in the meantime molecular diagnostic methods are also finding their uses in veterinary medicine, environmental analysis and foodstuff testing. Studies at pathology/cytology institutes or in the context of forensic questions represent a further field of use. However, in the meantime gene diagnostics is also being used in the health precautions field (e.g. testing of blood banks for freedom from infectious pathogens) and the legislature plans to demand such tests by law in the future. Methods which are also used in clinical molecular diagnostics (such as for example hybridization or amplification techniques such as the PCR (polymerase chain reaction), TMA (transcription mediated amplification), LCR (ligase chain reaction), bDNA (branched DNA) or NASBA (nucleic acid sequence based amplification) technology) are also among the routine procedures in fundamental scientific work.

In particular, through the determination of gene expression in tissues, nucleic acid analysis opens up very promising new possibilities in the study and diagnosis of tumor diseases. Thus for example the so-called microarray systems have opened up the possibility of determining the expression of hundreds or even thousands of genes in a single preparation. Here the sample material, purified nucleic acids, e.g. RNA or cDNA, is applied onto a chip which exhibits corresponding trapper oligonucleotides so that the nucleic acids in the sample can be detected by hybridization. As well as this, other methods for detecting nucleic acids in a sample, e.g. amplification methods such as the polymerase chain reaction (PCR), are also widespread.

A fundamental problem in nucleic acid analysis is sample preparation. The sample to be tested mostly contains cells or tissues with interfering, sometimes insoluble components (so-called debris), which can interfere with the subsequent isolation and analysis. Such insoluble components occur in particular in nucleic acid isolation from stools/feces, blood, warts, calcified structures (bones) or even strongly necrotic tissue samples. However, debris in the widest sense can also contain soluble components, e.g. released hemoglobin from erythrocytes which is present in extreme excess and must be separated from the nucleic acids during the isolation.

This problem is particularly serious in tumor diagnosis since here formalin-fixed paraffin sections (FFPE sections) are often used as sample material. During sampling from the patient, e.g. during biopsy or intraoperative sampling of tumor material, tissue material is fixed with formalin and embedded in paraffin in order to make the sample material storable. During the incubation, but also over years within the tissue block, extreme crosslinking of biomolecules (nucleic acids with proteins and in some cases proteins or nucleic acids with one another) due to the fixing agents takes place. These crosslinked structures within and outside the cells contribute to the formation of debris which is insoluble or lyzable with difficulty or not at all. Sections from the paraffin-embedded samples are usually prepared for assessment by pathologists, but these samples can also serve as starting materials in nucleic acid analysis. Here, in the purification of the nucleic acids after lysis, both cell debris and also the paraffin must be removed.

In addition, this problem with interfering, partially insoluble components (debris) also arises in the purification of nucleic acids from stool samples (feces, excrement). Stool samples consist firstly of the indigestible components of the diet (roughage) and undigested residues such as fat, starch, connective tissue and muscle fibers and water which were not absorbed in the upper colon sections. Among substances occurring naturally in the body, they contain discarded intestinal cells, residues of digestive enzymes and mucus. Further, small quantities of the bile acids themselves, and the lecithin and other phospholipids also secreted from the gall bladder for the protection of the intestinal mucosa are excreted together with the excrement.

In order to reduce costs and keep the processing time from sample receipt to determination of the analytical result as short as possible, it is a priority target to make methods for purifying nucleic acids as efficient as possible and as far as possible to perform them with automation. This applies particularly to diagnostics. Those methods which can be carried out in reaction vessels differing as little as possible and can be carried out in standardized formats (e.g. 96-well plate format) are well suited for automation since in these methods efficient pipetting robots can be used. Hence in the state of the art there is the need for simple, efficient and as far as possible automatable sample preparation.

Normal methods for nucleic acid purification comprise sample lysis under chaotropic conditions, purification by extraction, precipitation and purification from the liquid phase, e.g. the so-called phenol-chloroform extraction (see Sambrook et al., Molecular Cloning, A Laboratory Manual, 3rd Edition, Cold Spring Harbor Laboratory, Cold Spring Harbor Press, 2001, ISBN-13: 978-0879695774), or so-called column-based purification methods as for example disclosed in WO 2003040364-A1.

A standard method for the isolation of nucleic acids was described by Chomczynski (U.S. Pat. No. 5,346,994) and comprises the purification of nucleic acids from tissue material based on a separation from the liquid phase with the use of phenol and the chaotropic compound guanidine isothiocyanate. Here the sample must be homogenized in aqueous solution and centrifuged after addition of guanidine isothiocyanate (GTC) and phenol/chloroform. Proteins are in the organic phase, DNA in the inter-phase and RNA in the aqueous phase. The RNA can be precipitated from the aqueous phase. However, this method does not enable the reliable purification of RNA from FFPE tissue samples.

Other known methods for DNA or RNA isolation typically use chaotropic salts or phenol extraction.

EP0819696 discloses a method for the purification of nucleic acids which is based on the binding of nucleic acids to silica or other silicon dioxide derivatives under chaotropic conditions. Here the sample is lyzed in a chaotropic lysis buffer and the nucleic acids bound to a silica matrix.

Methods for the purification of nucleic acids from paraffin sections known in the state of the art firstly necessitate a costly dewaxing, wherein the paraffin is typically removed with xylene, and a costly subsequent rehydration with a xylene/ethanol dilution series.

Thus in WO 200146402 A1, a method for the purification of RNA from fixed paraffin sections is described, in which the paraffin section is first placed in an Eppendorf reaction vessel and dewaxed with xylene. Next the section must be rehydrated with a xylene/ethanol dilution series. Next for the purification of the RNA the sample is heated in a chaotropic solution for quite a long period (5 to 120 mins). Admittedly this method makes effective dewaxing possible, but it is costly and not very suitable for automation on account of the several centrifugation steps necessary.

Hence compared to the state of the art there is a need for improved methods for the purification of nucleic acids, and in particular for methods which are suitable for automation.

DEFINITIONS

The expression "biological sample" designates any sample which contains cells or cellular material, in particular cells, frozen cell pellets, fixed cells, feces/stools, "buffy coat" (=white blood cell fraction of the blood), ascites, swabs, in particular cheek or pharyngeal swabs, but quite especially uterine cervical swabs, sputum, organ needle biopsies, sperm, tissue samples, fixed tissue samples, tissue sections from fixed or non-fixed tissue samples, in particular frozen sections and paraffin sections, in particular formalin-fixed paraffin sections, tumor material, biopsy samples, blood samples, in particular whole blood or blood fractions, cell suspensions and in the broadest sense all samples which contain cell components, which is intended to include both intact cells and also cell components.

In addition, the expression "biological sample" also includes other nucleic acid-containing biological materials, such as for example blood serum or blood plasma, in particular virus-containing serum or plasma, and here quite especially HIV and HCV infected serum samples, secretions, spinal fluid, bile, lymph or urine. They can also be nucleic acid-containing materials that derive from biochemical or biotechnology processes and then have to be purified.

The term "cellular" relates both to prokaryotic and also to eukaryotic cells.

The term "lysis of the sample" comprises the disruption of the cells or cellular structures in the sample. It comprises in particular mechanical lysis methods (e.g. ultrasound), thermal lysis (e.g. freeze-thaw cycles, heating of the sample) and chemical lysis (e.g. with detergents). However, the expression "lysis of the sample" is not restricted to cells and can also relate to the release of nucleic acids with said method from non-cellular, biological structures or complexes.

The expression "nucleic acids" includes oligomeric and polymeric ribonucleotides and 2'-desoxyribonucleotides with a chain length of more than 10 monomer units. The monomer units in nucleic acids are linked via phosphate diester linkages between 3'- and 5'-hydroxy group adjacent monomer units and a heterocyclic base is bound glycosidically to the 1' atom of the given carbohydrate component. Nucleic acids can form double and triple strands by the formation of intermolecular hydrogen bridge bonds. Protein/nucleic acid complexes and nucleic acids with synthetic nucleotides, such as morpholinos, LNAs or PNAs are also meant.

The term "chaotropic conditions" designates solvent conditions in the presence of chaotropic agents or compounds. Chaotropic agents or compounds are compounds which modify or break up the secondary structure, tertiary structure and quaternary structure of proteins, nucleic acids and protein-nucleic acid complexes, while the primary structure remains intact. In solution under chaotropic conditions the intra-molecular interactions of biological molecules, in particular proteins, protein-nucleic acid complexes and nucleic acids, are broken up, as chaotropic compounds interfere with stabilizing intramolecular interactions in biological molecules, e.g. hydrogen bridge bonds, van der Waals forces and hydrophobic effects. Chaotropic compounds usually have large-volume ions which on account of their size can interfere with the intra-molecular hydrogen bridges and thereby lower the polarity of the solvent. As a result, the inter- and intramolecular interactions are broken up. Hence, many proteins precipitate, but the helical structure of double strand nucleic acid sections is still retained. By addition of chaotropic compounds to cell lysates or cell suspensions, proteins can be precipitated while nucleic acids remain in solution. Under chaotropic conditions, the binding of nucleic acids to silicon dioxide-based matrices is strongly favored. Chaotropic compounds for example include high molar concentration urea solutions (e.g. 6 to 8 mol/l urea), guanidinium salt solutions (e.g. 6 mol/l guanidinium chloride) and high molar concentration lithium salts (e.g. 4.5 mol/l lithium perchlorate). Chaotropic anions include the anions $F^-$, $PO_4^{3-}$, $SO_4^{2-}$, $CH_3COO^-$, $Cl^-$ and in particular $Br^-$, $I^-$, $NO_3^-$, $ClO_4^-$, $SCN^-$ and $Cl_3CCOO^-$. Chaotropic cations include the cations $Li^+$, $Mg^{2+}$, $Ca^{2+}$, $Ba^{2+}$, and in particular the guanidinium cation, $[CH_6N_3]^+$. Chaotropic compounds preferred for nucleic acid isolation are guanidinium isothiocyanate ($[CH_6N_3]^+SCN^-$) and guanidinium chloride.

The term "non-chaotropic conditions" designates solvent conditions in aqueous and/or alcoholic solution in the absence of chaotropic agents.

The term "purification of nucleic acids" describes the incomplete or complete removal of non-nucleic acid components from a nucleic acid-containing sample. It is not restricted to the attainment of a certain degree of purity.

The term "automated purification" includes methods which replace the manual labor of human personnel wholly or also only in some steps and in particular finds use in the steps of digestion of the biological body sample with a special buffer, the addition of magnetic particles or alternative binding methods, the incubation at a defined temperature, the removal of non-absorbed sample components, the washing steps, the elution of bound nucleic acids from the particles at a defined temperature and the separation of the eluate from the particle suspension.

The term "separation" includes the removal as far as possible of all biological or chemical substances or components which are not the actual target of the isolation, i.e. essentially not nucleic acids. In particular, the separation of these substances serves for the avoidance of interference or disrupting effects during the actual binding, enrichment, purification and subsequent detection of the target molecules.

The term "cell debris" includes all biological components which are not the primary target of a nucleic acid isolation and which are to be removed from the actual target molecules by a purification or negative selection step. After lysis of a cell sample, these include in particular cell components insoluble in aqueous solutions and difficult to lyze such as for example necrotizing tissue components, bone or calcareous structures, in particular microcalcifications, but also in addition ruptured or morphologically altered erythrocytes, warts and papilloma-like tissue structures, and also specific bacteria which have a complex, difficult to lyze sugar envelope (e.g. mycobacteria). In addition, it includes proteins, membrane components, in particular structures crosslinked by fixing, etc. In individual cases however it can also be components soluble in water, which are released after the lysis processes described above and have to be separated. One example is the hemoglobin released in large quantities and molar excess relative to nucleic acids after the lysis (e.g. owing to hypotonic buffer conditions) from erythrocytes which has to be separated before the further processing of the body sample.

In addition, "cell debris" in particular means all components in the feces/stools which are not nucleic acids. Stools consist firstly of the indigestible components of the diet (roughage) and undigested residues such as fat, starch, connective tissue and muscle fibers and water which were not absorbed in the upper colon sections. Substances occurring naturally in the body include discarded intestinal cells with nucleic acids which are to be isolated, residues of digestive enzymes and mucus. Further, small quantities of the bile acids themselves, and the lecithin and other phospholipids also secreted from the gall bladder for the protection of the intestinal mucosa are excreted together with the excrement.

The term "magnetic particles" includes both organic and also inorganic particles.

The term "silica" includes silicon dioxide and silicon dioxide derivatives, in particular $SiO_2$ crystals and other forms of $SiO_2$, e.g. diatoms constituted of $SiO_2$, zeolites, amorphous silicon dioxide, glass powder, silicic acid, waterglass and aluminum silicates and activated silicates.

The term "hydrophobic matrix" designates a solid phase whose surface is constituted of a hydrophobic material, in particular a hydrophobic plastic material, e.g. polyolefins, such as PP (polypropylene), PE (polyethylene), halogenated polyolefins, such as for example PTFE (polytetrafluoroethylene) and the like. The matrix can be present in any suitable form, e.g. in the form of particles, fibers, flat surfaces etc. In particular, the matrix can be in the shape of a vessel inner wall.

The term "lysis buffer system" implies a buffer system which contains at least one substance which can effect or favor the digestion of a cell, a cell system, cell components or other biological complexes or structures. The substances are particularly often selected from the group of detergents (Triton X-100, SDS or the like) and enzymatic reagents such as in particular proteinase K. Also included is the use of reagents from the group of aqueous, buffered or unbuffered solutions (in the simplest case water). One or more components from one or both groups together can be combined in one buffer system. In the context of this invention, reagents which contain chaotropic substances are expressly not meant as a component of the lysis buffer system in the first steps of a purification.

The further terms used in the present application have the usual meaning known to those skilled in the art.

SUMMARY OF THE INVENTION

The invention comprises methods for purifying nucleic acids from a biological sample which are characterized in that after taking up the sample in aqueous solution and after lysis of the sample, debris is separated from the sample under non-chaotropic conditions before the nucleic acids are then isolated from the lysate purified of debris.

The invention relates to a method for purifying nucleic acids from a biological sample, having the following steps:
a) taking up the sample in an aqueous solution;
b) lysing the sample;
c) separating from cell debris by suspending magnetic particles in the solution and use of a magnetic field for retaining the magnetic particles and separation of the magnetic particles from the solution; and
d) isolating the nucleic acids from the solution;
wherein steps (a) to (c) take place under non-chaotropic conditions.

The inventors have found that the separation of cell debris under non-chaotropic conditions advantageously simplifies the further isolation of the nucleic acids and in particular also leads to better automatability of the purification methods.

Expressed more generally, the invention relates to a method for purifying nucleic acids from a biological sample, having the following steps:
taking up the sample in an aqueous solution;
lysing the sample;
separating from cell debris; and
isolating the nucleic acids from the solution;
wherein steps (a) to (c) take place under non-chaotropic conditions.

According to one aspect of the present invention, step (c) comprises in particular the suspending of magnetic particles in the solution and use of a magnetic field for retaining the magnetic particles and separating the magnetic particles from the solution. In general, the addition of the particles could also advantageously be general, i.e. also non-magnetic particles instead of the magnetic particles (e.g. cellulose particles, ceramic particles or plastic particles), since they promote better aggregation of the debris.

According to one aspect of the invention, the magnetic particles have an average size of <50 µm, preferably <10 µm, quite preferably <0.5 µm, not excluding <0.1 µm, the size being determined by transmission electron microscopy methods.

According to one aspect of the invention, the magnetic particles have a silicon-containing coating, in particular a silicon dioxide-containing coating. Such magnetic particles are for example known from EP 1468430.

The magnetic particles preferably have a silica coating, i.e. are $SiO_2$-coated magnetic particles. The expression "$SiO_2$-coated magnetic particles" includes magnetite cores which consist of at least 90 weight percent $Fe_3O_4$ and the surface whereof is coated with silicate.

The magnetic particles are suspensible particles which by application of an external magnetic field can be immobilized in the magnetic field.

The separation of the magnetic particles from the solution is effected after immobilization of the particles by the magnetic field, and the solution can then be separated from the particles in any suitable way, e.g. by decantation, aspiration, etc.

The isolation of the nucleic acids from the sample according to step (d) can be effected by any suitable method, e.g. extraction methods, column-based methods, precipitation, etc. Step (d) of the isolation of the nucleic acids is not restricted to any defined purity level of the nucleic acids isolated.

In step (a), the sample is taken up in an aqueous solution. This can occur by mixing, suspension, emulsification or dissolution. Before or after taking up in the aqueous solution, the sample can be mechanically comminuted, for example by mechanical action (e.g. chopping or stirring), by the action of heat, by ultrasound treatment and similar processes. It is however also possible to suspend the intact tissue sample, e.g. a tissue section, directly in aqueous solution.

According to one aspect of the invention, the sample is a blood sample. In the complete lysis of blood, hemoglobin and also erythrocyte and leukocyte membrane components are liberated in large quantities and molar excess relative to the nucleic acids, and can be separated under step (c). Step (d) then serves only for the selective purification of the nucleic acids from the aqueous residual phase.

Alternatively, as already technically described, selective lysis of erythrocytes can be performed for example under hypotonic buffer conditions. During this, hemoglobin and erythrocyte membranes are liberated in large quantities and can be separated under step (c). In this case, the still necessary leukocyte lysis with release of the nucleic acids would be effected with addition of a chaotropic buffer and possibly proteinase K in step (d). These operating modes enable simple and complete automation of the extraction of nucleic acids from blood, in particular leukocytes, whereby costly process steps such as centrifugation and pelleting of the leukocytes and rejection of the supernatant can be avoided.

According to a further aspect of the invention, the sample is a stool/feces sample. In the lysis of stools, nucleic acids are released from excreted healthy or morbidly altered intestinal epithelial cells into a complex matrix of cell fragments, roughage, undigested food residues such as fat, starch, connective tissue and muscle fibers, residues of digestive enzymes and mucus, bile acids, lecithins and other phospholipids. All these components, which are not nucleic acids, can be wholly or partially separated under step (c). Step (d) then serves only for the selective purification of the nucleic acids from the aqueous residual phase.

According to one aspect of the invention, the biological sample is a paraffin-embedded sample, in particular a paraffin section and/or a fixed sample, in particular a formalin-fixed paraffin section.

The method according to the invention is particularly suitable for the workup of fixed samples, since fixed samples have an especially large amount of debris e.g. because of protein and nucleic acid crosslinking.

According to a preferred aspect of the invention, before step (d) the solution is heated to at least 50° C., preferably 50-95° C., preferably at least 60° C., and more preferably 60-80° C. This heating advantageously enables better suspension and better lysis of the biological sample in the aqueous solution. For more effective lysis, it is preferable to add a proteinase, in particular proteinase K.

According to one aspect of the invention, before step (c) the sample is again cooled to below 50° C. When paraffin is present in the sample the cooling to below 50° C. has the additional advantage that the paraffin solidifies again, e.g. in the form of a paraffin ring on the vessel wall. The sample or the lysate can then for example be aspirated very simply and accurately with a pipette tip with no blockage problems, while the paraffin remains in the reaction vessel in the form of the paraffin ring described.

According to a further aspect of the invention, the sample or the lysate is brought into contact with a hydrophobic matrix, in that for example it is taken up in a vessel of hydrophobic plastic material. This is particularly preferred in the workup of paraffin-containing samples. As the hydrophobic matrix, for example the known reaction vessels from Eppendorf or Sarstedt, which consist of polyolefins (e.g. polypropylene and polyethylene) are suitable for this. It is particularly preferred to heat paraffin-containing samples in contact with a hydrophobic matrix to over 50° C. before step (d), since as a result the paraffin melts and on cooling advantageously deposits as a ring on the liquid surface on the matrix, e.g. in the case of a plastic reaction vessel on the edge of the vessel. This occurs through adsorption processes of the liquefied paraffin on the hydrophobic matrix. In the following steps, because of this, the liquid sample can then advantageously be aspirated accurately without blockages of pipette tips, while the paraffin ring remains in the reaction vessel.

According to a further aspect of the invention, the process described is so good as regards purification efficiency that for most applications a single 3-20 µm, quite especially preferably a single 10 µm paraffin section suffices for obtaining very high yields of nucleic acids. As a result, the quantity of paraffin used is below critical quantities which prevent or interfere with formation of the ring.

According to one aspect of the invention, in step (c) the solution is separated by aspiration of the magnetic particles.

According to one aspect of the invention, step (d) further includes the addition of a chaotropic compound to the solution. Thereby, the initial or repeated addition of proteinase K (if in step (a) proteinase K was already used) in step (d), i.e. before or after the addition of the chaotropic solution, is not excluded.

According to one aspect of the present invention, step (d) further includes the addition of unused (fresh) magnetic particles with a silicon-containing coating to the solution.

For the isolation of RNA it is preferable to add a DNase in biologically effective quantity to the sample. Thereby, DNA is "digested" and goes into solution, while the undigested RNA can be isolated from the solution. The DNase digestion can be performed at different times during the extraction, at the earliest after the lysis and at the latest after the elution at the end of the purification.

For the purification of DNA it is preferable to add an RNase in biologically effective quantity to the sample, whereby RNA is digested and the intact DNA can be isolated from the solution. The RNase digestion can be performed at different times during the extraction, at the earliest after the lysis and at the latest after the elution at the end of the purification.

However, it is preferable to perform the DNA detection in the presence of the RNA purified together with it, i.e. with omission of the RNase step or with the use of buffer conditions which enable a selective isolation of DNA with exclusion of the RNA.

The invention further includes the use of magnetic particles for the removal of cell debris from a biological sample in an aqueous solution under non-chaotropic conditions. In particular, the magnetic particles with a silicon-containing coating can be magnetic particles with a silica-containing coating.

Below, the invention is described by means of detailed examples in combination with the figures, in which the following is shown.

In standard methods for nucleic acid purification, the sample material is taken up or lyzed in a chaotropic buffer.

The present invention is based on the surprising discovery that a nucleic acid purification leads to better results when cell debris is removed from the sample under non-chaotropic conditions before the isolation of the nucleic acids. This can for example be effected by centrifugation or filtration. According to one embodiment of the invention, the debris is removed by means of magnetic particles under non-chaotropic conditions. Preferably these particles have a silicon-containing coating, in particular a silicon dioxide-containing coating. Such particles are known from EP 1468430, which is incorporated herein by reference. The preparation of such particles is described in detail below.

The isolation of nucleic acids from the lysate purified of debris can be effected by known methods. For example extraction protocols which are based on purification from chaotropic solutions, e.g. by precipitation of the nucleic acids and/or absorption on silica-containing matrices under chaotropic conditions, are suitable. In known column-based methods, the nucleic acids are bound from the lysate onto a silica membrane in the presence of chaotropic salts which are added in high concentration, and eluted from the membrane after a purific-ation step. Suitable kits are commercially available from QIAGEN GmbH, Hilden, German Federal Republic.

According to a preferred aspect of the invention, the isolation of the nucleic acids is effected by a renewed use of (fresh) silica-coated magnetic particles under chaotropic conditions.

According to a preferred aspect of the invention, the separation of debris or interfering substances also makes it possible to increase the purification efficiency, reproducibility and robustness, and to reduce outliers and ambiguous or unclear results in the analysis of the nucleic acids ("flagging" of results, "flagged" results). In clinical diagnostics, where such methods are also intended to be used as well as in research, this is attended by so-called repetition or reflex tests, which signify additional and avoidable costs.

EXAMPLES

Materials and Methods

The following materials and methods were used in all the following examples.

As starting materials, tumor samples from a clinical pathology laboratory are used, which were fixed in formalin when taken and then embedded in paraffin. These methods for fixing and embedding are generally known to those skilled in the art and are not described in more detail here. Tissue sections, e.g. with a thickness of 5 to 10 μm, are obtained from the sample with a microtome and transferred into a 1.5 ml sample vessel, e.g. a 1.5 ml polypropylene sample vessel. Alternatively, samples which have already been applied onto a microscope slide can also be detached from this with a razor blade or in another suitable way (e.g. dewaxing with ethanol/xylene) or scratched off and transferred into the sample vessel.

As well as the commercially available "Versant kPCR Sample Preparation Reagents" from Siemens Healthcare Diagnostics GmbH (Erlangen, Germany) (consisting of a proteinase K solution, binding buffer (contains chaotrope, e.g. 59% guanidine thiocyanate and 10% octyl-phenoxypoly-ethoxyethanol), silica-coated magnetic particles, as for example known from EP 1468430, washing buffer 1 (contains chaotrope or 36% guanidine thiocyanate and 30% ethanol, washing buffer 2 (contains 80% ethanol), washing buffer 3 (contains 5-chloro-2-methyl-4-isothiazolin-3-one and 2-methyl-4-isothiazolin-3-one (3:1)) and elution buffer (contains sodium azide), the following buffers were used:

1. FFPE lysis buffer
   10 mM Tris HCl
   0.1 mM EDTA
   2% SDS
   pH 8.0
2. DNA-free DNAse solution (Ambion, Cat# A 1906, Ambion, Foster City, Calif. 94404, USA)

Instead of the buffer of the commercially available "Versant kPCR Sample Preparation Reagents" from Siemens Healthcare Diagnostics GmbH, other common buffer compositions known to those skilled in the art can also be selected. In particular, detergent-containing and/or hypotonic buffers are possible as FFPE lysis buffers. Suitable washing buffers are also known from the state of the art and are commercially available. Chaotropic buffer compositions are possible as binding buffers for the subsequent isolation of nucleic acids from the lysate with silica-coated beads, e.g. 4.5M guanidium HCl, 6M guanidinium isothiocyanate and the like. The requirements to be set for suitable washing buffers consist only in that the buffer must ensure that the nucleic acid is not detached from the silica matrix. In general, a high alcohol content and optionally slightly alkaline pH suffices to prevent the autoproteolysis of the DNA. Washing buffers which contain chaotropic compounds are also suitable, provided they fulfill the aforesaid conditions. Also possible as elution buffers are the buffer compositions known to those skilled in the art, e.g. TE buffer (10 mM Tris HCl, 0.1 mM EDTA, pH 8.0).

Attention is drawn to the fact that in this and similar purification protocols the RNA can fragment into 100 to 500 base pair-long fragments, however fragmented RNA is also well suited to expression analysis with current methods (RT-PCR, Micro-Array, and the like).

The (relative) RNA yield quantification was effected by means of the one-step kinetic real-time reverse transcriptase polymerase chain reaction (One-Step kRT-PCR) using a Taq-Man probe. For the analysis of the RNA yield, the CT value (cycle threshold, i.e. the value of the amplification cycle which first exceeds a defined threshold value) was determined for the RNA of the reference or housekeeping gene RPL37A, i.e. the mRNA of the human gene for ribosomal protein L37a, Gene Bank Accession Number NM_000998. The q RT-PCR was performed using the "Super-Script™ one-step with a Platinum® Taq kits" from Invitrogen, Karlsruhe, Germany, and using primers and a probe from Eurogentec, Cologne, Germany.

For performing a kRT-PCR expression analysis of RPL37A, 1 μl of purified RNA was added to 9 μl of Master-mix, consisting of 400 nM forward primer, 400 nM reverse primer, 200 nM Taqman probe (FAM/TAMRA labeled), reaction mix with 0.2 mM of each dNTP and 1.2 mM magnesium sulfate and 1 μl of Platinum® Taq Mix. The reaction was performed on an ABI7900 instrument from Applied Biosystems, Applera Deutschland GmbH, Darmstadt, Germany, with the following temperature profile:
   30 mins at 50° C.
   2 mins at 95° C.
   15 secs at 95° C.
   30 secs at 60° C., 40 cycles.

For the determination of the CT values, the software SDS 2.0 from Applied Biosystems was used according to the operating instructions. The CT value corresponds to the number of amplification cycles beyond which the amplification signal has exceeded a defined threshold, e.g. the measurement threshold. Accordingly, the more transcript is present in the sample, the smaller the CT value is. In some cases, for better representation the CT values for RPL37A were stated as 40-CT in the figures. In this way, the values are inverted and higher 40-CT values correspond to higher expression values of RPL37A. If not specified in more detail, the directly measured CT value is meant.

Example 1

Purification of nucleic acids from paraffin section samples with removal of debris by centrifugation under non-chaotropic conditions.

RNA from FFPE sections was manually purified as follows:
Centrifuge FFPE section in an Eppendorf sample vessel for 1 min at maximum speed;
Take up the paraffin section in 150 µl of FFPE lysis buffer and 50 µl of proteinase K solution;
Incubation for 2 hours at 65° C. with shaking;
Centrifugation (e.g. 5 mins at 10,000 g) at room temperature, careful transfer of the liquid supernatant into a fresh sample vessel (thus separating from debris and paraffin residues);
Addition of 800 µl of binding buffer and thorough mixing of the solution;
Addition of 50 µl of a suspension of magnetic particles and thorough mixing of the solution; Incubation for 15 mins at room temperature with shaking;
Application of a magnetic field, aspiration and rejection of the supernatant;
Removal of the magnetic field. Uptake and suspension of the magnetic particles (with the nucleic acids bound thereon) in 850 µl of washing buffer 1;
Application of the magnetic field, aspiration and rejection of the supernatant;
Removal of the magnetic field. Uptake and suspension of the magnetic particles (with the nucleic acids bound thereon) in 450 µl of washing buffer 2;
Application of the magnetic field, aspiration and rejection of the supernatant;
Removal of the magnetic field. Uptake and suspension of the magnetic particles (with the nucleic acids bound thereon) in 450 µl of washing buffer 3;
Repeated washing with washing buffer 3;
After application of the magnetic field and removal of the supernatant, uptake of the sample in 100 µl of elution buffer, incubation for 10 mins at 70° C. with shaking in a thermomixer;
Application of a magnetic field, transfer of the eluate into a fresh sample vessel;
Addition of 10 µl of 10×DNAse buffer and 1 µl of DNAseI;
Incubate for 30 mins at 37° C.
Freezing of the samples and/or further analysis of the eluates.

Example 2

Isolation of RNA from a formalin-fixed paraffin section samples with removal of debris by addition of magnetic particles under non-chaotropic conditions.

Figure 1:
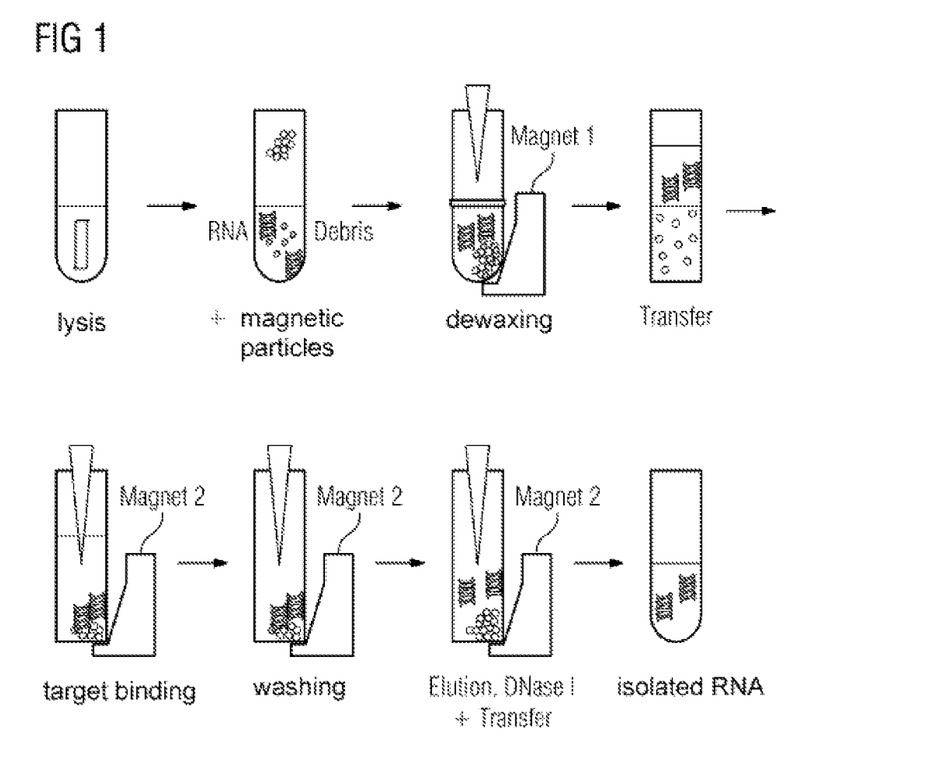
FIG. 1: A schematic representation of one embodiment of the method according to the invention (either manual or automated).

This method corresponds to the method shown schematically in FIG. 1.

RNA from FFPE sections was manually purified as follows:
Centrifuge FFPE section in an Eppendorf sample vessel for 1 min at maximum speed;
Addition of 150 µl of FFPE lysis buffer and 50 µl of proteinase K solution;
Incubate for 2 hours at 65° C. with shaking;
Addition of 50 µl of magnetic particles;
Mixing by 2 mins shaking;
Magnetize sample;
Carefully transfer supernatant into a new vessel (cell debris and paraffin residues remain in the old vessel);
Addition of 800 µl of binding buffer (chaotrope);
Addition of 50 µl of magnetic particles;
Incubation for 15 mins at room temperature with shaking;
Application of a magnetic field, aspiration and rejection of the supernatant;
Removal of the magnetic field. Uptake and suspension of the magnetic particles (with the nucleic acids bound thereon) in 850 µl of washing buffer 1;
Application of the magnetic field, aspiration and rejection of the supernatant;
Removal of the magnetic field. Uptake and suspension of the magnetic particles (with the nucleic acids bound thereon) in 450 µl of washing buffer 2;
Application of the magnetic field, aspiration and rejection of the supernatant;
Removal of the magnetic field. Uptake and suspension of the magnetic particles (with the nucleic acids bound thereon) in 450 µl of washing buffer 3;
Repeated washing with washing buffer 3;
After application of the magnetic field and removal of the supernatant, uptake of the sample in 100 µl of elution buffer, incubation for 10 mins at 70° C. with shaking in a thermomixer;
Application of a magnetic field, transfer of the eluate into a fresh sample vessel; Addition of 10 µl of 10×DNAse buffer and 1 µl of DNAseI;
Incubate for 30 mins at 37° C.
Freezing of the samples and/or further analysis of the eluates.

The method according to the invention is shown schematically in FIG. 1. It can be run manually or automated.

Example 3

Automated purification of RNA from formalin-fixed paraffin sections.

RNA from formalin-fixed paraffin sections was purified with the use of the following automated protocol on a Siemens Plattform VERSANT kPCR (extraction unit). Up to 48 tissue sections can be purified in one pass.

Sample Preparation

Tissue sections (5-10 µl) were pelleted by centrifuging at room temperature and placed on sample holders of the Siemens Plattform VERSANT kPCR, where all hardware modules (heater/shaker, magnets, etc.), sample vessels, buffers and pipette tips are placed at their designated positions.

Start of Purification Program:
Addition of 150 µl of lysis buffer to samples;
Addition of 50 µl of proteinase K solution;
Transfer of the sample vessels to a heater/shaker and incubation for 2 hrs at 65° C. with shaking;
Transfer of the lysate to a deep-well sample plate (DWP);
Addition of 600 µl of binding buffer (chaotrope);
Addition of 50 µl of magnetic particle suspension into the DWP;
Incubation for 10 mins at room temperature with shaking;
Transfer of the DWP to magnet;
Incubation for 5 mins at room temperature in the magnetic field;
Aspiration and rejection of the supernatant;
Transfer of the DWP from the magnet to the heater/shaker;
Addition of 850 µl of washing buffer 1;
10 secs shaking at room temperature;

Transfer of the DWP to the magnet;
Magnetization for 2 mins at room temperature;
Aspiration and rejection of the supernatant;
Transfer of the DWP from the magnet to the heater/shaker;
Addition of 450 μl of washing buffer 2;
10 secs shaking at room temperature;
Transfer of the DWP to the magnet;
Magnetization for 2 mins at room temperature;
Aspiration and rejection of the supernatant;
Transfer of the DWP from the magnet to the heater/shaker;
Addition of 850 μl of washing buffer 3;
10 secs shaking at room temperature;
Transfer of the DWP to the magnet;
Magnetization for 2 mins at room temperature;
Aspiration and rejection of the supernatant;
Addition of 100 μl of elution buffer;
Transfer of the DWP from the magnet to the heater/shaker;
Incubation for 10 mins at 70° C. with shaking;
Transfer of the DWP to the magnet;
Addition of 12 μl of DNase-Mix (10 μl 10× of DNase buffer; 2 μl of DNase 1);
Transfer of the DWP from the magnet to the heater/shaker (cooled down to 37° C.);
Incubation for 30 mins at 37° C. without shaking;
Transfer of the DWP to magnet;
Transfer of the DNase-digested samples to 1.5 ml sample vessels;
End of Purification Program
Freezing of the samples and/or further analysis of the eluates.

Example 4

Automated purification of RNA from formalin-fixed tissue sections with the use of an additional binding step with magnetic particles for separation of cell debris under non-chaotropic conditions.

FIG. 1 shows the schematic representation of the method according to the invention.

RNA from formalin-fixed paraffin sections was purified with the use of the following automated protocol on a Siemens Plattform VERSANT kPCR (extraction unit). Up to 48 tissue sections can be purified in one pass.

Sample Preparation

Tissue sections (5-10 μm) were pelleted by centrifuging at room temperature and placed on sample holders of the Siemens Plattform VERSANT kPCR, where all hardware modules (heater/shaker, magnets, etc.), sample vessels, buffers and pipette tips are placed at their designated positions.

Start of Purification Program:
Addition of 150 μl of lysis buffer to samples;
Addition of 50 μl of proteinase K solution;
Transfer of the sample vessels to a heater/shaker and incubation for 2 hrs at 65° C. with shaking;
Addition of 50 μl of magnetic particle suspension;
Incubation for 10 mins at 65° C. with shaking;
Incubation for 5 mins without shaking;
Transfer of the sample tubes from the heater/shaker to a magnet
Magnetization of the samples for 3 mins;
Transfer of the sample lysate to a deep-well sample plate (DWP);
Addition of 600 μl of binding buffer (chaotrope);
Addition of 50 μl of magnetic particle suspension into the DWP;
Incubation for 10 mins at room temperature with shaking;
Transfer of the DWP to magnet;
Incubation for 5 mins at room temperature in the magnetic field;
Aspiration and rejection of the supernatant;
Transfer of the DWP from the magnet to the heater/shaker;
Addition of 850 μl of washing buffer 1;
10 secs shaking at room temperature;
Transfer of the DWP to the magnet;
Magnetization for 2 mins at room temperature;
Aspiration and rejection of the supernatant;
Transfer of the DWP from the magnet to the heater/shaker;
Addition of 450 μl of washing buffer 2;
10 secs shaking at room temperature;
Transfer of the DWP to the magnet;
Magnetization for 2 mins at room temperature;
Aspiration and rejection of the supernatant;
Transfer of the DWP from the magnet to the heater/shaker;
Addition of 850 μl of washing buffer 3;
10 secs shaking at room temperature;
Transfer of the DWP to the magnet;
Magnetization for 2 mins at room temperature;
Aspiration and rejection of the supernatant;
Addition of 100 μl of elution buffer;
Transfer of the DWP from the magnet to the heater/shaker;
Incubation for 10 mins at 70° C. with shaking;
Transfer of the DWP to the magnet;
Addition of 12 μl of DNase-Mix (10 μl 10× of DNase buffer; 2 μl of DNase 1);
Transfer of the DWP from the magnet to the heater/shaker (cooled down to 37° C.);
Incubation for 30 mins at 37° C. without shaking;
Transfer of the DWP to magnet;
Transfer of the DNase-digested samples to 1.5 ml sample vessels;
End of Purification Program
Freezing of the samples and/or further analysis of the eluates.

Figure 2:
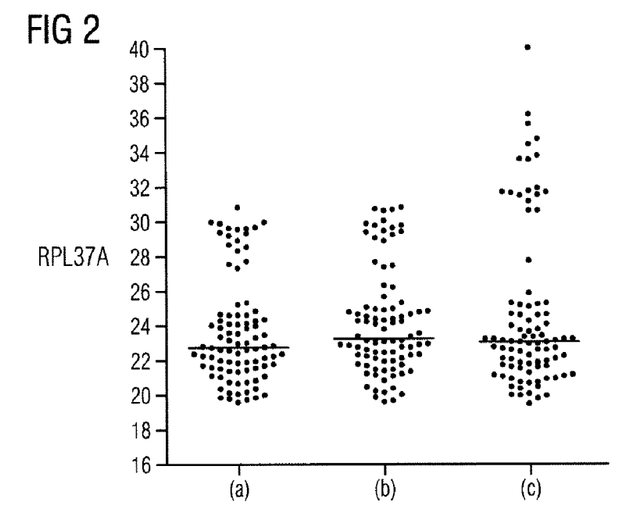
FIG. 2: A comparison of yield between a first manually performed method according to the invention with removal of debris by centrifugation (a), a second automatically performed method according to the invention with removal of debris by magnetic particles (b), and a method according to the state of the art (Qiagen RNeasy FFPE Kit) without prior removal of debris (c).

FIG. 2 shows a comparison of yield (the lower the CT value for RPL37A, the higher this is) between a first manually performed method according to the invention with removal of debris by centrifugation (a), a second automatically performed method according to the invention with removal of debris by magnetic particles (b), and a manual method according to the state of the art (c) (Qiagen RNeasy FFPE Kit, Qiagen GmbH, Hilden, Germany, method as per manufacturer's directions).

Figure 3:
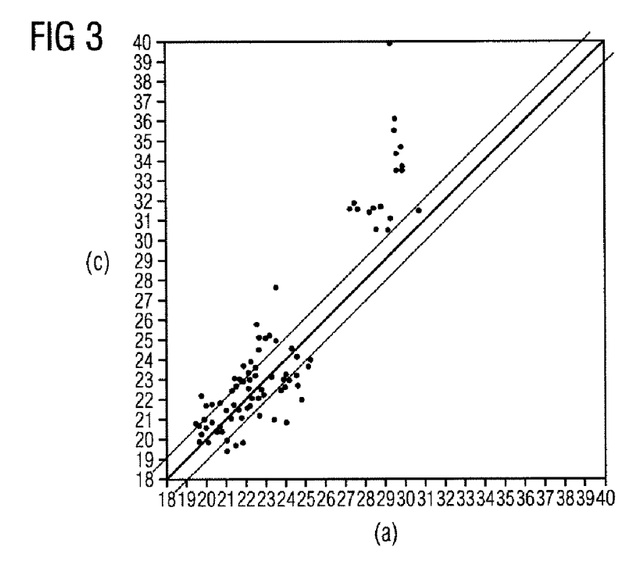
FIG. 3: A comparison (correlation) of yield between a first manually performed method according to the invention with removal of debris by centrifugation (a) and a method according to the state of the art (Qiagen RNeasy FFPE Kit) without prior removal of debris (c).

FIG. 3 shows a correlation of yield (the lower the CT value for RPL37A, the higher the expression of the gene) between a method according to the state of the art (Qiagen RNeasy FFPE Kit, (c)) and a manually performed method according to the invention with removal of debris by centrifugation (a).

Example 5

Comparison of the yields after purification with the methods described in Examples 1 and 2.

This example illustrates the effect of the removal of cell debris by an additional purification step with magnetic particles (Example 2) or by centrifugation (Example 1). In addition, samples where the cell debris was not removed before the addition of chaotropic buffer were purified. The subsequent steps were performed identically, as described in Example 1, for all samples.

Figure 4:
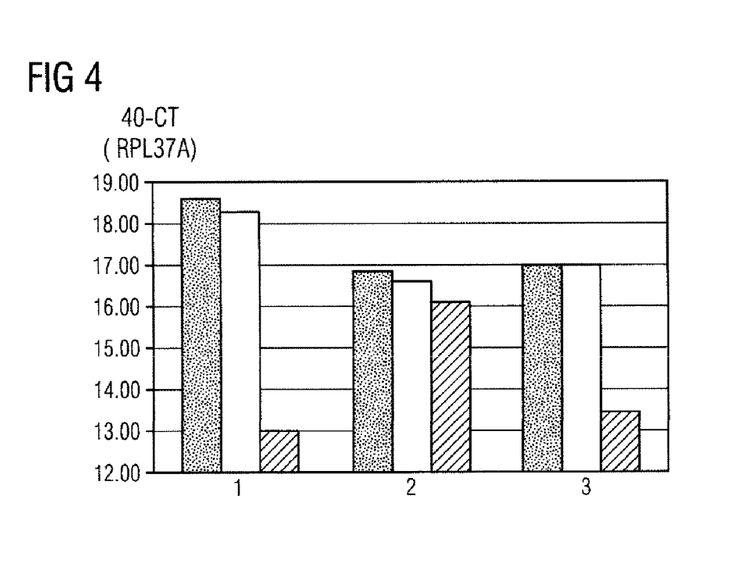
FIG. 4: A comparison of yield from 2 manual purific-ations by the method according to the invention with centrifugation or with an additional bead binding step for debris and by a manual method according to the state of the art.

FIG. 4 shows a comparison of the yield of a manual purification by the method according to the invention with centrifugation according to Example 1 (dotted bars), with an additional bead binding step for debris according to Example (white bars) and by a manual method according to the state of the art without removal of cell debris (hatched bars).

In FIG. 4, results for 3 different tissue samples ("1", "2" and "3") are shown. It is found that the purification with the removal of cell debris according to the invention leads to a significantly higher yield compared to samples wherein the cell debris was not removed. The yield comparison was made by quantitative PCR of the housekeeping gene RPL37A, 40-CT (CT=cycle threshold, i.e. the number of amplification cycles at which the measurement threshold of the system is exceeded) as a statement of the transcript quantity. A difference of 3 to 5 CT values of RPL37A corresponds to a yield loss of a factor of 8 to 32 of the total RNA. This leads to the conclusion that on the one hand unlyzed tissue or cell debris impairs the efficient and quantitative purification of nucleic acids, in particular of RNA, and presumably interferes with the binding of nucleic acids to silica-coated magnetic particles under chaotropic conditions. Furthermore, it is shown that the initial centrifugation step under non-chaotropic conditions for the removal of cell debris can be replaced by an additional purification step with silica-coated magnetic particles under non-chaotropic conditions. This has the considerable advantage that the method is thus very much simpler to automate, since no further centrifugation steps are necessary.

Example 6

Comparison of the yield from the automated purification with and without binding of cell debris by means of silica-coated magnetic particles according to the Examples 3 and 4 described.

This experiment illustrates the effect of the removal of cell debris by an additional purification step with silica-coated magnetic particles (corresponding to Example 4) in comparison to the automated purification without additional purification from cell debris with magnetic particles under non-chaotropic conditions (corresponding to Example 3). For each of the two processes, 3 successive sections from 7 different tissue samples ("A" to "G") were used and analyzed as regards the expression of RPL37A.

Figure 5:
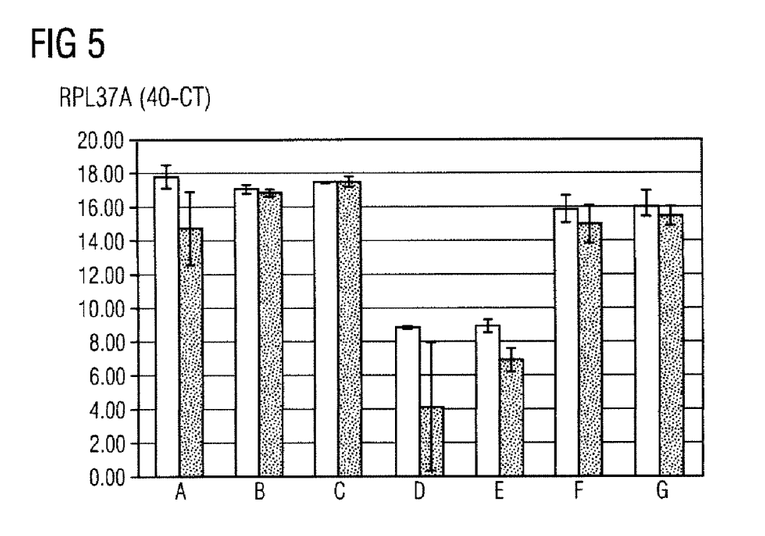
FIG. 5: Comparison of the automated method according to the invention with an automated method from the state of the art.

FIG. 5 shows the RNA yield in the comparison of the automated method according to the invention (corresponding to Example 4; white columns) with an automated method from the state of the art (corresponding to Example 3; dotted columns) for 7 different samples (A-G). It is found that the additional magnetic purification step led to better yields in 5 out of 7 cases and this step also led to more reproducible results between the 3 successive sections from one tissue sample (smaller variance within different RNA preparations from the same paraffin block).

Example 7

Effect of tissue binding on the efficiency and interference-free pipettability of the automated purification.

The VERSANT kPCR system from Siemens, which contains a pipetting robot from Hamilton, enables the control of all aspiration and dispensing steps for each individual pipetting step. The liquid movements are recorded via pressure sensors which are contained in the individual pipetting channels. These changes in the pressure conditions during each pipetting step are recorded over time (=TADM total aspiration and dispense monitoring). For each pipetting step, certain tolerance ranges for the change in the pressure conditions can be defined. As soon as the TADM profile lies outside the defined range, it can be directly recorded that the pipetting step for one sample was not properly performed, whether this was caused by blockage of the tips, lack of liquid, foaming in the liquid or other negative influences. The sample can thereupon be labeled for further analyzes or also possibly be excluded from a further analysis. In clinical diagnostics, this information would in many cases lead to a reflex or repetition test, either on the same system or an alternative method.

Figure 6:
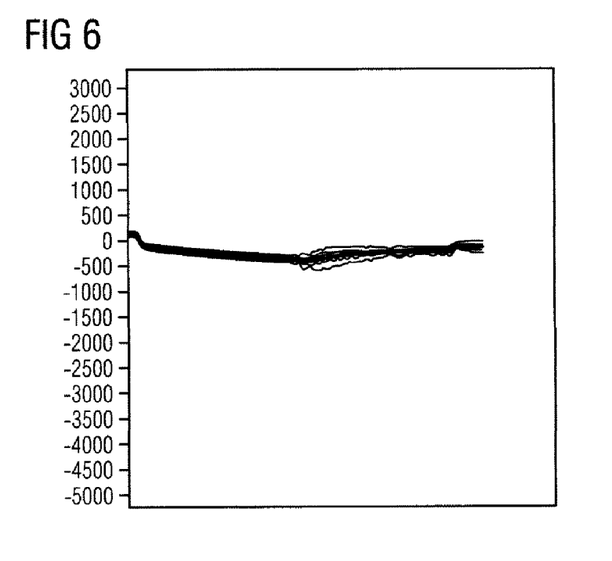
FIG. 6: Total aspiration and dispense monitoring (TADM) curves according to the automated process according to the invention.
Figure 7:
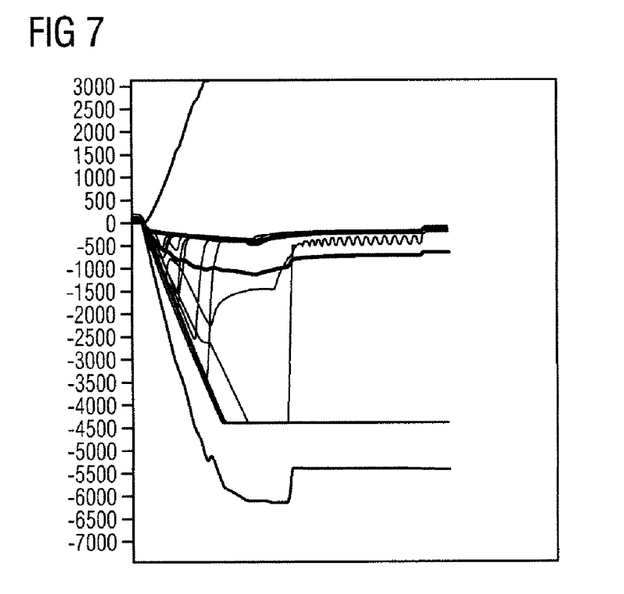
FIG. 7: Total aspiration and dispense monitoring (TADM) curves according to an automated process according to the state of the art.

FIGS. 6 and 7 show TADM profiles for the aspiration of the lysates from fixed paraffin sections for the transfer into a new vessel for the nucleic acid binding under chaotropic conditions. These TADM profiles correspond to the pressure variation with time in the pipette for this pipetting step of each individual sample. The closer together the individual curves lie, the more consistent, i.e. controllable, the pressure variation is in the use of a certain method. This example concerns firstly samples (corresponding to Example 4) for which magnetic particles were previously added for the removal of cell debris (FIG. 6) and secondly samples (corresponding to Example 3) for which no addition of particles or separation of debris took place (FIG. 7). In contrast to FIG. 6, FIG. 7 shows a very much more uneven TADM profile. This can in particular be explained in that with these samples cell debris was still contained in the lysate, which can lead to blockage of the tips and hence to the occurrence of very high pressure. In many cases, with automated methods without prior removal of the cell debris, interruption of the course of the process can even occur. This can be effectively prevented by the method according to the invention. When magnetic particles are used in the method according to the invention for the removal of cell debris, this has the additional advantage that in the debris removal step the same hardware can be used that is also used for the isolation of nucleic acids with magnetic particles under chaotropic conditions.

This example shows that through the removal of cell debris, the pipettability (e.g. aspiration of the lysate) and efficiency of the automated purification is improved, since exclusion of a sample on account of a poor TADM profile occurs more seldom. As a result, in clinical diagnostics the number of reflex tests (repeat performance of the test which leads to a result) is markedly reduced which is accompanied by a cost reduction.

Example 8

Purification of nucleic acids from blood samples.

The method according to the invention is also particularly suitable for the purification of nucleic acids from blood samples, since it enables improved removal of hemoglobin or erythrocyte fragments from the blood. According to the invention, erythrocytes, erythrocyte fragments and also released hemoglobin, which can interfere with subsequent process steps, are firstly efficiently removed from the sample under non-chaotropic conditions.

According to a first modification, 400 μl of lysis buffer (e.g. 10 mMol Tris HCl, 0.1 mMol EDTA, 2% SDS, pH 8.0) are added to a blood sample (e.g. 100 μl EDTA whole blood). Next, addition of 50 μl of magnetic particle suspension (e.g. uncoated or silica-coated magnetic particles) to the sample, incubation at room temperature for 10 mins and separation of the particles by application of a magnetic field take place. Next, as described above, nucleic acids can be isolated under chaotropic conditions from the sample taken.

According to a second modification, the blood sample is taken up in a hypotonic lysis buffer (e.g. 25 mM Tris HCl, pH 7.5, 10 mM KCl, 5 mM $MgCl_2$), incubated briefly to lyze the erythrocytes and then the addition of magnetic particle suspension (e.g. uncoated or silica-coated magnetic particles) to the sample, incubation at room temperature for 10 mins and separation of the particles together with the erythrocyte fragments and the hemoglobin by application of a magnetic field take place. Next, the lysis of the leukocytes is effected under chaotropic conditions, i.e. release of the nucleic acids and binding of these to freshly added silica-coated magnetic particles. Proteinase K can optionally be introduced before or simultaneously with the chaotropic reagent.

Example 9

Preparation of Silica-Coated Magnetic Particles

The preparation of silica-coated magnetic particles can for example be effected by silica coating of magnetite particles. The magnetites used are preferably hydrophilic, commercially available iron oxide ($Fe_3O_4$), which are preferably available with narrow particle size distribution and spherical morphology. Magnetite particles are commercially available, such products are for example manufactured by Bayer AG under the product name BAYOXIDE E. Suitable types are obtainable under the designation BAYOXIDE E8706, E8707, E8709 and E8710. Similar products are also marketed by BASF under the name "Magnetic Pigment 340" or "345". Although good results can be achieved with all the products named, the type BAYOXIDE E 8707 or E 8706 is preferably used. This magnetic pigment has a spherical morphology with an average particle diameter of 0.2 μm and a narrow particle size distribution (ca. 0.1 to 0.7 μm). As starting materials for the introduction of silicate groups, both alkali metal silicates (sodium or potassium waterglasses) and also silica sols can be used. Suitable waterglasses, which usually have very high pH values (13-14), are offered by various firms, for example Merck or Cognis. The material to be coated, for example Bayoxide E 8707, can be added to a dilute for example 1% waterglass solution with stirring. After an incubation of ca. 30 minutes, it is filtered off, washed with water and dried. According to one example protocol, 50 g of Bayoxide E 8707 are added with stirring to 1000 ml of an aqueous 0.25% waterglass solution (HK30, Cognis) and the mixture is then stirred for a further 30 mins at RT. The particles are filtered off, washed 5 times with water and once with ethanol and then dried for 5 hrs at 80° C.

The invention claimed is:

1. A method for purifying nucleic acids from a biological sample, having the following steps:
 a) taking up the sample in an aqueous solution;
 b) lysing the sample;
 c) separating cell debris comprising proteins and membrane components from the sample by suspending magnetic particles in the solution binding the cell debris to the suspended magnetic particles and using a magnetic field for retaining and separating the magnetic particles and the bound cell debris from the solution; and
 d) isolating the nucleic acids from the solution; characterized in that steps (a) to (c) take place under non-chaotropic conditions;
 further characterized in that the solution is heated to at least 50° C. before step (d).

2. The method as claimed in claim 1, characterized in that the magnetic particles have an average size of <50 μm.

3. The method as claimed in claim 2, characterized in that the magnetic particles have a silicon-containing coating.

4. The method as claimed in claim 2, characterized in that step (d) further includes the addition of a chaotropic compound to the sample.

5. The method as claimed in claim 4, characterized in that step (d) further includes the addition of unused magnetic particles with a silicon-containing coating to the solution.

6. The method as claimed in claim 2, wherein said silicon-containing coating is a silicon dioxide-containing coating.

7. The method as claimed in claim 1, characterized in that the sample is a blood sample.

8. The method as claimed in claim 1, characterized in that the biological sample is a paraffin-embedded sample and/or a fixed sample.

9. The method as claimed in claim 1, characterized in that after the heating the sample is cooled to below 50° C. before step (d).

10. The method as claimed in claim 1, characterized in that the sample is brought into contact with a hydrophobic matrix in at least one of steps (a), (b) and (c).

11. The method as claimed in claim 1, characterized in that the solution is heated to at least 60° C. before step (d).

12. The method as claimed in claim 11, characterized in that after the heating the sample is cooled to below 50° C. before step (d).

13. The method as claimed in claim 1, characterized in that the solution is heated to 60-95° C. before step (d).

14. The method as claimed in claim 13, characterized in that after the heating the sample is cooled to below 50° C. before step (d).

* * * * *